United States Patent [19]

Kerkenaar et al.

[11] Patent Number: 4,958,016
[45] Date of Patent: Sep. 18, 1990

[54] BIFUNCTIONAL OLIGOSACCHARIDES AND ALSO ACTIVE COMPOUNDS DERIVED THEREFROM

[75] Inventors: Antonius Kerkenaar, Blaricum; Diederik J. M. Schmedding, Driebergen; Ronald T. M. Van Den Dool, Culemborg, all of Netherlands

[73] Assignee: Nederlandse Organisatie Voor Toegepast-Natuurwetenschappelijk Onderzoek Tno, The Hague, Netherlands

[21] Appl. No.: 202,788

[22] Filed: Jun. 3, 1988

[30] Foreign Application Priority Data

Jun. 9, 1987 [NL] Netherlands ............... 8701342

[51] Int. Cl.$^5$ ............... C07H 1/00; C12N 9/88; C12N 1/20; C12N 1/00
[52] U.S. Cl. ............... 536/123; 536/114; 435/101; 435/232; 435/252.31; 435/835
[58] Field of Search ............... 435/101, 835, 252.31; 536/114, 123

[56] References Cited

U.S. PATENT DOCUMENTS 4,607,025 8/1986 Petitou et al. ............... 514/53

OTHER PUBLICATIONS

R. C. Caswell et al., "Detection of Alginate Lyases by Isoelectric Focusing and Activity Staining", *International Journal of Biological Macromolecules, Structure Function and Interactions*, vol. 8, No. 6, Dec. 1986, pp. 337–341, Butterworths & Co. (Publishers) Ltd.
P. E. Jansson et al., "Structural Studies of Gellan Gum, An Extracellular Polysaccharide Elaborated by Pseudomonas elodea", *Carbohydrate Research*, vol. 124, 1983, pp. 135–139, Elsevier Science Publishers B.V., Amsterdam, N.L.
R. I. Hollingsworth et al., "Bacteriophage–Induced Acidic Heteropolysaccharide Lyases that Convert the Acidic Heteropolysaccharides of Rhizobium Trifolii Into Oligosaccharide Units", *Journal of Bacteriology*, vol. 160, No. 2, Nov. 1984, pp. 510–516, American Society for Microbiology.
R. J. Linhardt et al., Review, Polysaccharide Lyases, Applied Biochemistry and Biotechnology, vol. 12, 1986, pp. 135–176, The Human Press, Inc.

*Primary Examiner*—Ronald W. Griffin
*Assistant Examiner*—Pamela S. Webber
*Attorney, Agent, or Firm*—Rosen, Dainow & Jacobs

[57] ABSTRACT

Bifunctional oligosaccharides, characterized by the formula

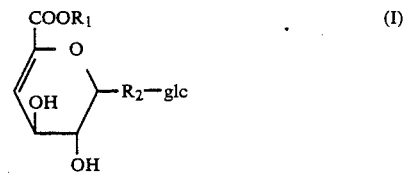

wherein $R_1$ represents a hydrogen atom, an alkyl group having 1–4 carbon atoms or an alkali metal, $R_2$ represents a single bond or a divalent radical compound of monosaccharides and glc represents glucose, are obtained with the help of a specific microbial lyase cleaving the glucose-glucoronic acid bond in polysaccharides; said bifunctional oligosaccharides can be reacted with all kinds of products like proteins and drugs resulting in products having modified properties like solubility etc.

6 Claims, No Drawings

BIFUNCTIONAL OLIGOSACCHARIDES AND ALSO ACTIVE COMPOUNDS DERIVED THEREFROM

The invention relates to bifunctional oligosaccharides which contain a terminal $\Delta^{4,5}$-uronic acid group at the non-reducing end.

From Applied Biochemistry and Biotechnology, 12 (1986), pages 135–176, a variety of polysaccharide lyases are known which are able to cleave the respective uronic- acid-containing polysaccharides into $\Delta^{4,5}$-uronic-acid-containing oligosaccharides. Such lyases are usually of microbial origin and are isolated both from pathogenic and non-pathogenic bacteria and fungi. Examples of such lyases are, inter alia, heparin, chondroitin, pectin, pectate and alginate lyases which cleave the corresponding substrates at specific positions. More particularly, for example, (a) heparin lyase cleaves the -4)-α-D-GlcNSO$_{\overline{3}}$-(6-SO$_{\overline{4}}$)-(1-/-4)-α-L-IdUA (2-SO$_{\overline{4}}$)-(1- bond in heparin and (b) pectate lyase cleaves the -4)-α-D-GalUA(1-/-4)-α-D-GalUA-(1- bond in pectate, where GlcNSO$_{\overline{3}}$ represents 2-deoxy-2-sulphaminoglycopyranose, IdUA represents idopyranosyluronic acid and GalUA represents galactopyranosyluronic acid.

The unsaturated oligosaccharides obtained by means of the lyases are interesting compounds because of the acrylate function introduced at the non-reducing end of the oligosaccharide with the reducing end being left intact. Through the agency of said acrylate function, it is possible to couple by means of a Michael addition a variety of compounds containing nucleophilic groups to such $\Delta^{4,5}$-uronic-acid-containing oligosaccharides.

For example, pharmacologically active compounds having a uronic acid structure are known from U.S. Pat. No. 4,607,025. These compounds advantageously have the formula

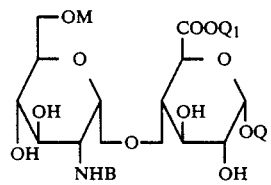

in which M represents a hydrogen atom or an SO$_3$M$_1$ group in which M$_1$ represents a cation, B represents a hydrogen atom or a functional group such as an acetyl or sulphate group, Q$_1$ represents a hydrogen atom, an alkyl group containing 1–4 carbon atoms or a cation, and Q represents an alkyl group containing 1–4 carbon atoms or an aryl group.

Surprisingly, a microbial lyase has now been found with which it is possible to cleave the glucoseglucuronic acid bond in polysaccharides to form $\Delta^{4,5}$-glucuronic-acid-containing oligosaccharides. As a microbial source for the lyase according to the invention, mention may be made of bacteria, bacteriophages, moulds, etc.

The invention therefore relates in the first place to oligosaccharides having the formula 1

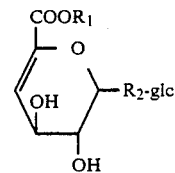

in which
R$_1$ represents a hydrogen atom, an alkyl group containing 1–4 carbon atoms or an alkali metal,
R$_2$ represents a single bond or a divalent radical composed of monosaccharides and
glc represents glucose.

As examples of the symbol R$_2$, mention is made of divalent radicals composed of 1–5 monosaccharides which have been chosen from the group consisting of glucose, mannose, galactose, arabinose, bructose, xylose, rhamnose, uronic acids and derivatives thereof, such as acetates, pyruvates, amines and sulphates.

Uronic acids are understood to mean glucuronic acid, galacturonic acid, iduronic acid, mannuronic acid and guluronic acid. Advantageously, R$_2$ represents a -glc-rha- radical in which rha represents the methylpentose rhamnose.

Furthermore, the symbol R$_1$ advantageously represents a hydrogen atom, a methyl group or a sodium atom.

Furthermore, the invention relates to a method for preparing the oligosaccharides having the formula 1 by subjecting a polysaccharide having the formula [glucuronic acid-R$_2$-glucose]$_n$, where n has the value 2 or over, for example 2-5000, and R$_2$ has the abovementioned meaning, to the action of the respective lyase which cleaves the glucose-glucuronic acid bond and is preferably obtained from a bacteria strain of the Bacillus genus. Advantageously use is made of the *Bacillus circulans* strain, preferably the strain which is deposited at the National Collection of Industrial Bacteria (NCIB), Scotland under the number NCIB 12482.

As polysaccharide having the formula [glucuronic acid-R$_2$-glucose]$_n$, use may be made, for example, of the commercially available "Gelrite" which has the formula [glucuronic acid-glucose-rhamnose-glucose]$_n$, where n has approximately the value 1500. Said polysaccharide has, inter alia, the advantage that because of the high antigen determinant action of rhamnose, important pharmacological applications of the active substances based on the oligosaccharides according to the invention derived therefrom are possible, which active substances can be prepared in a relatively simple manner through the agency of the acrylate function of the $\Delta^{4,5}$-glucuronic acid radical. Another example of a polysaccharide which can be used in the invention is gellan gum which is Gelrite acetylated in the 6 position of one of the two glucose residues which occur in the tetramer (P. E. Janson, B. Lindberg and P. A. Sandfort, Carbohydrate Research 124 (1983), pages 135–139).

The activity of the lyase according to the invention which cleaves the glucose-glucuronic acid bond can be checked and followed by the increase in absorption at 229 nm. Said increase in absorption can be ascribed to the conjugated carboxy alkene system produced under the influence of said lyase in the oligosaccharide formed having the above formula 1.

In pursuance of the above reference to active compounds, a wide variety of active compounds such as glycoproteins and glycolipids having the formula 2

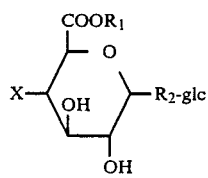

in which $R_1$, $R_2$ and glc have the above-mentioned meaning and X represents an $R_3O$, $R_3S$-, $R_3NH$- or $R_3N(R_4)$ group, where $R_3$ and $R_4$ denote an optionally (poly)cyclic and/or possibly unsaturated hydrocarbon radical which is optionally interrupted by one or more hetero atoms, can be prepared on the basis of the oligosaccharides according to the invention through the agency of a Michael addition. Examples of compounds which can be reacted with the oligosaccharides according to the invention are thiols such as cysteine and cysteine-containing proteins, and also pharmacological thiol compounds such as captopril and sparcomycin.

Addition of proteins to the oligosaccharides according to the invention modifies such proteins and this has an influence on the stability, solubility (in the case of lipophilic proteins) and retention in membrane reactors as a result of the increase in the molecular mass. Said modification leaves the reducing end of the saccharide intact in contrast to natural glycoproteins and this provides these artificial glycoconjugates with unexpected properties. In the same manner, drug derivatives can also be modified and this results in modified physical properties (solubility, size, charge etc.,) or modified chemical properties (target-oriented drugs) of the respective drugs.

Furthermore, the oligosaccharides according to the invention can be used in the preparation of vaccines. More particularly, in that case suitable cell walls (polysaccharides) of pathogenic organisms can be cleaved by means of the present lyase and the oligosaccharides thus obtained can be processed to form vaccines.

The invention is explained by means of the examples below; these examples should not be interpreted as restrictive.

EXAMPLE 1

Method for preparing the tetramer: $\Delta^{4,5}$-glucuronic acid-glucose-rhamnose-glucose from Gelrite.

Stage 1. Preparation of the Gelrite lyase

The organism which is used to isolate this enzyme is deposited in the National Collection of Industrial Bacteria in Scotland under the number NCIB 12482. This organism was cultured aerobically at 30° C. on a G medium having the following composition:

| Composition of G medium: | | |
|---|---|---|
| Gelrite | 5 g/l | |
| $K_2HPO_4$ | 4 g/l | |
| $KH_2PO_4$ | 1 g/l | |
| $(NH_4)_2 SO_4$ | 1 g/l | |
| $Mg SO_4.7H_2O$ | 0.5 g/l | |
| NaCl | 0.5 g/l | Final pH = 7.0 |

The cell material for the production of the Gelrite lyase was obtained by culturing the above-mentioned microorganism (3% inoculation) on the abovementioned G medium in a stirred reactor with a working capacity of 1.5. After an incubation time of approx. 18 hours, the cells were centrifuged (30 min at 9000 ×g).

The oligosaccharides and salts in the supernatant were separated from the enzyme by means of ultrafiltration (PM10 filter in the "mini-tan" of 10 millipore). After washing a few times with 4 mM tris (pH=7.8) solution, this yielded an enzyme solution of approx. 140 units per liter (U/l) which appeared to be stable in the frozen state.

The activity of the Gelrite lyase enzyme obtained was measured on the basis of increase in extinction at 229 nm due to the formation of the $\Delta^{4,5}$-uronic acid group. On the basis of NMR and elementary analysis and measured at a pH of 7, the extinction coefficient (E) of the tetramer was approximately $E_{229}$ 5600 $M^{-1}$ $cm^{-1}$.

To measure the Gelrite lyase activity, 100 μl of enzyme solution was added to a mixture of 200 μl of 50 mM tris-HCl, pH=7.8, 500 μl of 2 g/l gelled Gelrite and 200 μl of water. One enzyme unit gave a change in extinction at 229 nm of 5.6 per minute.

Stage 2. Method for the batchwise preparation of the unsaturated $\Delta^{4,5}$-glucuronic acid-glucose-rhamnoseglucose tetramer To prepare 5.2 g of $\Delta^{4,5}$-tetramer, the Gelrite lyase solution (8.1 units in total) was incubated for 17 hours at 30° C. with a Gelrite solution (2.0 g/l) in 4 mM tris-HCl, pH 7.8.

The dosing of enzyme was such that 2.5 units of enzyme activity was added per gram of Gelrite. It was found that the extinction (229 nm) of the effluent was approximately 14 (theoretical maximum $E^{229} \approx 15$).

Then enzyme and unreacted Gelrite were separated from each other by means of ultrafiltration (cut off 10,000). It was found that the enzyme still had 72% of the original activity, and it was again incubated with a fresh Gelrite solution (2.5 U/g Gelrite). The ultrafiltrate of the first enzyme conversion was pooled with that of the second and third enzyme conversions. In this manner, 3.2 g of Gelrite was first converted and then 2 g and 1 g of Gelrite. After the ultrafiltration, the tetramer was purified from positively charged particles, such as tris, by passing the product through an Amberlite $IR_{120}$ column (eluent $H_2O$). Since the pH of the effluent was approx. 3, the pH thereof was adjusted to 7 by adding 1 M NaOH so that the Na salt was obtained. After freeze-drying, the dry weight was 5.2 g, which corresponds to a yield of 83%. In addition to the unsaturated tetramer, the product obtained was found to contain a few salts but no octamer. On the basis of the extinction, the production rate was approximately 2 g/l/day.

If 20 g/l Gelrite and about 5 enzyme units per gram of Gelrite are used at 48° C., the production rate can be increased to approx. 290 g/l/day.

EXAMPLE II

Method for preparing the unsaturated $\Delta^{4,5}$-glucuronic acid- glucose-rhamnose-glucose tetramer.

Stage 1. Preparation of Gelrite lyase

The method of preparing the Gelrite lyase was carried out in the same manner as in Example I.

Stage 2. The continuous conversion of Gelrite into the unsaturated $\Delta^{4,5}$-glucuronic acid-glucoserhamnose-glucose tetramer In this stage, 18.4 g of Gelrite was converted in a reactor having a working capacity of 4.6 by 134 units of Gelrite lyase at pH 7.8 (5 mM tris-HCl) and 30° C. The liquid from the reactor was pumped continuously through an ultrafiltration unit (Millipore minitan with PM 10 filter). For the first 4 hours of the reaction, the permeate was returned until the extinction (229 nm) was approximately 18. Then the substrate (4 g/l of Gelrite in 5 mM tris-HCl, pH 7.8) was pumped into the reactor just as fast as the permeate was removed (D=0.075 h$^{-1}$). After a total of 32 g of Gelrite had been pumped into the reactor, the supply pump was turned off and the reactor was emptied by pumping via the ultrafiltration unit. The extinction of the permeate was found to be 18.4, and this corresponds to approximately 60% conversion. In this manner, 26.8 g of product were obtained which contained approximately 85% unsaturated tetramer and 5% of unsaturated octamer (based on extinction).

The production rate was 4.1 g/l/day with a Gelrite concentration of 4 g/l and an enzyme dosing of 4.2 U/g Gelrite.

We claim:

1. Oligosaccharides, characterized by the formula 1

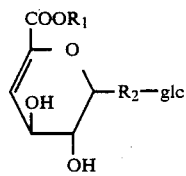

in which
R$_1$ represents a hydrogen atom, an alkyl group containing 1-4 carbon atoms or an alkali metal,
R$_2$ denotes a single bond or a divalent radical composed of monosaccharides, and
glc represents glucose.

2. Oligosaccharides according to claim 1, characterized by formula 1, in which R$_1$ represents the meaning stated in claim 1 and R$_2$ denotes a radical containing 1–5 monosaccharides selected from the group consisting of glucose, mannose, galactose, arabinose, bructose, xylose, rhamnose, uronic acids and derivatives thereof selected from the group consisting of acetates, pyruvates, amines and sulphates.

3. Oligosaccharide according to claim 2 in which R$_2$ represents a glc-rha group.

4. A process for preparing oligosaccharides by means of converting polysaccharides by means of a lyase, characterized in that a polysaccharide having the formula [glucuronic acid-R$_2$-glucose]$_n$, in which n has the value 2 or over, and R$_2$ has the meaning stated in claim 2, is converted with a microbial lyase which cleaves the glucose-glucuronic acid bond.

5. The process according to claim 4, characterized in that a lyase is used which is isolated from the *Bacillus circulans* strain deposited at the National Collection of Industrial Bacteria under the number NCIB 12482.

6. Compounds characterized by the formula 2

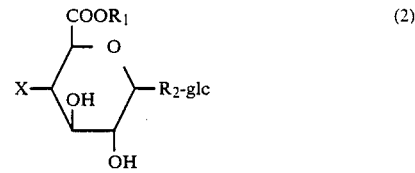

in which
R$_1$ and R$_2$ have the meaning stated in claim 2 and
X is an active radical selected group consisting of R$_3$O, R$_3$S-, R$_3$NH- and R$_3$N(R$_4$)-, where R$_3$ and R$_4$ represent a polycyclic group or an unsaturated hydrocarbon which may be interrupted by one or more hetero atoms.

* * * * *